United States Patent [19]

Noguchi et al.

[11] Patent Number: 5,041,733

[45] Date of Patent: Aug. 20, 1991

[54] METHOD AND APPARATUS FOR IDENTIFYING CHROMOSOMES OR CELLS

[75] Inventors: Yoshio Noguchi; Yoshinobu Uchibori; Mikio Yamashita, all of Tsukuba, Japan

[73] Assignee: Agency of Industrial Science & Technology, Tokyo, Japan

[21] Appl. No.: 161,064

[22] Filed: Feb. 26, 1988

[30] Foreign Application Priority Data

Mar. 20, 1987 [JP] Japan .................................. 62-66240
Mar. 27, 1987 [JP] Japan .................................. 62-75707

[51] Int. Cl.$^5$ .......................................... G01N 21/64
[52] U.S. Cl. .............................. 250/461.2; 250/459.1
[58] Field of Search ............... 250/458.1, 459.1, 461.1, 250/461.2

[56] References Cited

U.S. PATENT DOCUMENTS 4,284,412  8/1981  Hansen et al. .................. 250/459.1
4,596,036  6/1986  Norgren et al. ....................... 382/6
4,778,593 10/1988  Yamashita et al. ............. 250/461.2

OTHER PUBLICATIONS

Dean, P. N. et al., "High Resolution Dual Laser Flow Cytometry", *J. Histochem. Cytochem.*, vol. 26, pp. 622-627 (1978).
Lebo, R. V. et al., "High-Resolution Chromosome Sorting and DNA Spot-Blot Analysis Assign McArdle's Syndrome to Chromosome II", *Science*, vol. 225, pp. 57-59 (1984).
Wheeless, L. L., "Slit-Scanning and Pulse Width Analysis", In: Melamed, M. R. et al., *Flow Cytometry and Sorting* (New York, John Wiley & Sons, 1979) pp. 125-135.
Cambier, J. L., et al., "A Multidimensional Slit-Scan Flow System", *J. Histochem. Cytochem.*, vol. 27, pp. 321-324 (1979).
Norgren, R. M. et al., "Restoration of Profiles from Slit-Scan Flow Cytometry", *IEEE Transactions on Biomedical Engineering*, vol. BME-29, pp. 101-106 (1982).

*Primary Examiner*—Jack I. Berman
*Assistant Examiner*—Richard Hanig
*Attorney, Agent, or Firm*—Armstrong, Nikaido, Marmelstein, Kubovcik, & Murray

[57] ABSTRACT

A method and an apparatus for sorting chromosomes or cells by utilizing a difference in fluorescent profile-patterns. A linear laser beam having a high beam intensity is formed from several fringe patterns, and fluoresence intensities from local portions of chromosome or cell are measured in real-time. Resolution of chromosome or cell is improved. A type of flowing chromosome or cell which permits the rotational conditions within a range can be sorted accurately and rapidly.

7 Claims, 10 Drawing Sheets

METHOD AND APPARATUS FOR IDENTIFYING CHROMOSOMES OR CELLS

BACKGROUND OF THE INVENTION

1. Field of the Invention

The present invention relates to an apparatus and a method in which differences in fluorescence intensity at narrow strips of local portions of individual chromosome or cell flowing through a flow chamber are measured, so that chromosomes or cells of a specific type are sorted and collected on the basis of patterns of the differences

2. Description of the Prior Art

In order to classify chromosomes or cells of a specific type, various methods have been used in the fields of medical science, biology and the like Heretofore, such a method in which chromosomes are classified in accordance with parameters relating to the shape of a chromosome such as a size of the chromosome, e.g., a length of a long-arm portion or a short-arm portion of the chromosome, centrometric index and the like on the basis of the image by an optical microscope has been adopted as a method for classifying chromosomes. However, such a method in which a chromosome in a cell is stained with quinacrine mustard, and a type of chromosomes is identified on the basis of a difference in patterns of fluorescent lateral fringes (Q-band) which indicate characteristic features of the chromosome was discovered by T. Casperson in Sweden in 1970 A method for staining chromosome according to the above described method is called as Q-differential staining. Other than this Q-differential staining, C-differential staining and G-differential staining were discovered and by which a type of chromosome is classified on the basis of a difference in lateral fringes of a higher fluorescence intensity which are called as C-band and G-band differing from Q-band. As described above, at present various chromosome types can be accurately and fully identified on the basis of a difference in fluorescent band patterns appearing on a chromosome.

In order to identify gene of eucaryote, a method for making clear genes of individual chromosomes is employed by the properties of genes contained in the chromosome of a respective type. For this purpose, it is required to collect only a large amount of gene of a specific type in living conditions. Furthermore, in the fields of tumorlogy and immunology, it becomes necessary to collect a large amount of only cells of a specific type such as subgroup of lymphocyte in living conditions.

As a method for classifying cells, there are a method in which morphologic characteristic features of cells or differences in physical properties of cells are skillfully utilized, and a method in which differences in surface membrane of cells are utilized. Moreover, such a method in which the surface of a cell is labelled with a specific fluorescent material to identify a variant of the cell by means of fluorescence microscope has been effected In addition to the methods as described above, such a manner that a device called as a cell sorter begins to spread with rapidity In the cell sorter, cells or chromosomes which have been previously labelled with a fluorescent material, flow through a flow chamber or in a jet stream from a flow chamber nozzle at a high-speed. These cells or chromosomes are irradiated with a laser beam, and a fluorescent intensities of the chromosomes or cells as a result of the irradiation is measured, and the measured fluorescent intensities are analyzed, whereby specific chromosomes or cells are collected and sorted. This method is of a special importance in the fields of cytochemistry, immunology, tumorlogy, genetics, molecular biology and the like.

Nevertheless, in a conventional cell sorter, cells or chromosomes have been irradiated with a laser beam having a far larger section than that of a size of the cells or chromosomes flowing through a tube-shaped aqueous solution, so that the intensity of fluorescence emitted from the cells or chromosomes which had been previously labelled as a result of the irradiation has been measured Therefore, a conventional apparatus is called as a zero-resolution apparatus. In these circumstances, the differences in fluorescence intensity derived from local points of cells or chromosomes could not be identified. For this reason, cells or chromosomes of a limited specific type could not be sorted and collected.

For instance, a method which is utilizing a dual beam apparatus has been proposed by P. N. Dean et al. ("High Resolution Dual Laser Flow Cytometry", J. Histochem. Cytochem , Vol. 26, pp. 622-627, 1978.) In this method, LLL 761 chromosomes derived from human pellicle cell are broken up into pieces, then these are stained with fluorescent materials of Hoechst 3325Z and Chromomycin A3, and thus the stained pieces are irradiated with two laser beams of ultraviolet light and visible light, whereby fourteen types of chromosomes are uniquely identified in accordance with such high resolution analysis. However, human ninth to twelfth chromosomes could not be sorted and collected by means of a conventional cell sorter and even the dual beam apparatus.

Then, R. V. Lebo et al., indicated that the human ninth chromosome can be separated from a group of the human tenth to twelveth choromosomes by labelling the human chromosomes with two kinds dyes of DIPI and chromomycin (R. V. Lebo et al., "Science," Vol. 225, 6 July, 1984, pp. 57-59). However, the human tenth to twelfth chromosomes can not be separated and collected by means of a conventional cell sorter.

As a method for improving a resolution power of a conventional flow cytometer, it is important to narrow the width of a laser beam L. L. Wheeless et al., and Cambier et al., have developed the apparatuses in which the maximum radius of cell nucleus of a flowing cell and the size of the cell are measured. (L. L. Wheeless: "Slit-Scanning and Pulse Width Analysis", pp. 125-135, in Flow Cytometry and Sorting, John Wiley and Sons, 1979. J. L. Cambier et al.: "A Multidimensional Slit-Scan Flow System", J. Histochem. Cytochem., pp. 321-324, 1979)

However, in the above-mentioned apparatuses, since the slit width is wide, when a chromosome or cell passes through the flow chamber the variation of the size of chromosome or cell with time is not measured every moment, but only the maximum radius of chromosome or cell at the time of passage is measured.

On the other hand, a research group in the Lawrence Livermore National Laboratory has developed a method for narrowing laser beam in which two laser beams are interefered and the obtained fringe-pattern is used (Norgren et al.: "Resoration of Profiles from Slit-Scan Flow Cytometry", IEEE Transactions on Biomedical Engineering, Vol. BME-29, pp. 101-106

(1982)). For example, according to the Young interference method and the Mach-Zehnder interference method, a vertical fringe pattern can be formed. Furthermore, a ring-shaped fringe pattern can be formed in accordance with the Fabry-Perot interference method.

A method in which flowing chromosomes at a high-speed are irradiated with a fringe pattern formed in accordance with the Mach-Zehnder interference method is known by Richard M. Norgren et al., U.S. Pat. No. 4,596,036 "Method and Apparatus for Fringe-Scanning Chromosome Analysis".

In the method of R. M. Norgren et al., however, since flowing chromosomes are irradiated with laser beams of a pattern having several fringes and a high beam intensity, the measurement of such fluorescence intensity emitted by several laser beams of vertical fringes means to measure the total amount of the fluorescence intensity. Accordingly, it is concluded that the fluorescence intensity emitted from the local portions of the vertical fringe of chromosome can not be obtained so far as data as to the total amount of fluorescence intensity are analyzed. For this reason, it was impossible to measure a fluorescent band pattern, a length and the like of chromosome in real-time in accordance with conventional methods.

In this connection, a development for an apparatus and a method for sorting and collecting a specific cell or chromosome while maintaining biological activity on the basis of differences in local fluorescence intensity of chromosome or cell has been strongly desired.

SUMMARY OF THE INVENTION

An object of the present invention is to provide an apparatus by which a fluorescent band pattern of flowing chromosomes or a length of chromosome can be measured in real-time.

Another object of the present invention is to provide an apparatus by which differences in fluorescence intensity derived from tens of local portions of individual cell or chromosome can be identified.

A further object of the present invention is to provide a method in which differences of the fluorescence intensity in band patterns derived from local portions of flowing chromosomes or cells are identified, and chromosomes or cells of a specific type which could not have been heretofore sorted are collected.

In the first aspect of the present invention, an apparatus for identifying a chromosome or cell comprises:

a means for flowing an aqueous suspension containing chromosomes or cells which have been previously labelled with fluorescent materials;

an irradiation means provided with a laser beam source, an interference means wherein a part of laser beams emitted from the laser beam source is branched, and the laser beam branched is combined again with the emitted beams to form laser beams having a fringe pattern of lateral fringe perpendicular to a flow axis along which the chromosomes or cells flow, an optical means converting interference laser beams having the fringe pattern into elliptical beams in which a direction of the flow axis is flat, and a slit for allowing only one interference fringe contained in the interference beams to pass therethrough to irradiate the chromosomes or cells with the laser beam containing only the single interference fringe;

a fluorescence measuring means for measuring an intensity of fluorescence emitted from the chromosomes or cells due to the irradiation; and an identifying means for detecting the signal output from the fluorescence measuring means to identify chromosome or cell of a specific type.

Here, a dimension of the slit in the flow axis direction may be 0.6 to 1.5 $\mu$m with respect to the direction of the flow axis.

A breadth of the slit may be 50 to 300 $\mu$m.

The irradiation means may be provided with two laser beam sources.

The laser beams forming a crossing angle of 45° with each other in a plane perpendicular to the flow axis may be emitted from the two laser beam sources In the second aspect of the present invention, an apparatus for identifying a chromosome or cell comprises:

a means for flowing a liquid containing chromosomes or cells at a high-speed;

a means for emitting light onto the chromosomes or cells flowing through the flowing means;

a fluorescence measuring means for measuring fluorescence-intensity emitted from a fluorescent material with which the chromosomes or cells have been previously labelled;

a discriminating means wherein a fluorescent profile-pattern obtained from variation of the fluorescent intensity with time is compared with a plurality of the preset standard fluorescent profile-patterns of chromosome or cell; and a sorting means for sorting the chromosomes or cells on the basis of the comparison of the fluorescent profile-pattern with the preset standard fluorescent profile-patterns by the discriminating means.

Here, the standard profile-pattern may include a profile-pattern relating to a rotating condition of chromosomes or cells.

In the third aspect of the present invention, a method for identifying a chromosome or cell comprises the steps of:

irradiating a flow-stream containing chromosomes or cells which have been previously labelled with a fluorescent material with a laser beam of only one interference fringe among interference laser beams having a fringe pattern perpendicular to a flow axis along which the chromosomes or cells flow;

measuring fluorescence intensity emitted from the fluorescent material on the chromosomes or cells;

comparing a fluorescent profile-pattern obtained from variation of the fluorescent intensity with time with preset standard fluorescent profile-patterns of chromosome or cell; and sorting the chromosomes or cells on the basis of the comparison of the fluorescent profile-pattern with the preset standard fluorescent profile-patterns The above and other objects, effects, features and advantages of the present invention will become more apparent from the following description of preferred embodiments thereof taken in conjunction with the accompanying drawings.

DETAILED DESCRIPTION OF PREFERRED EMBODIMENTS

Figure 1:
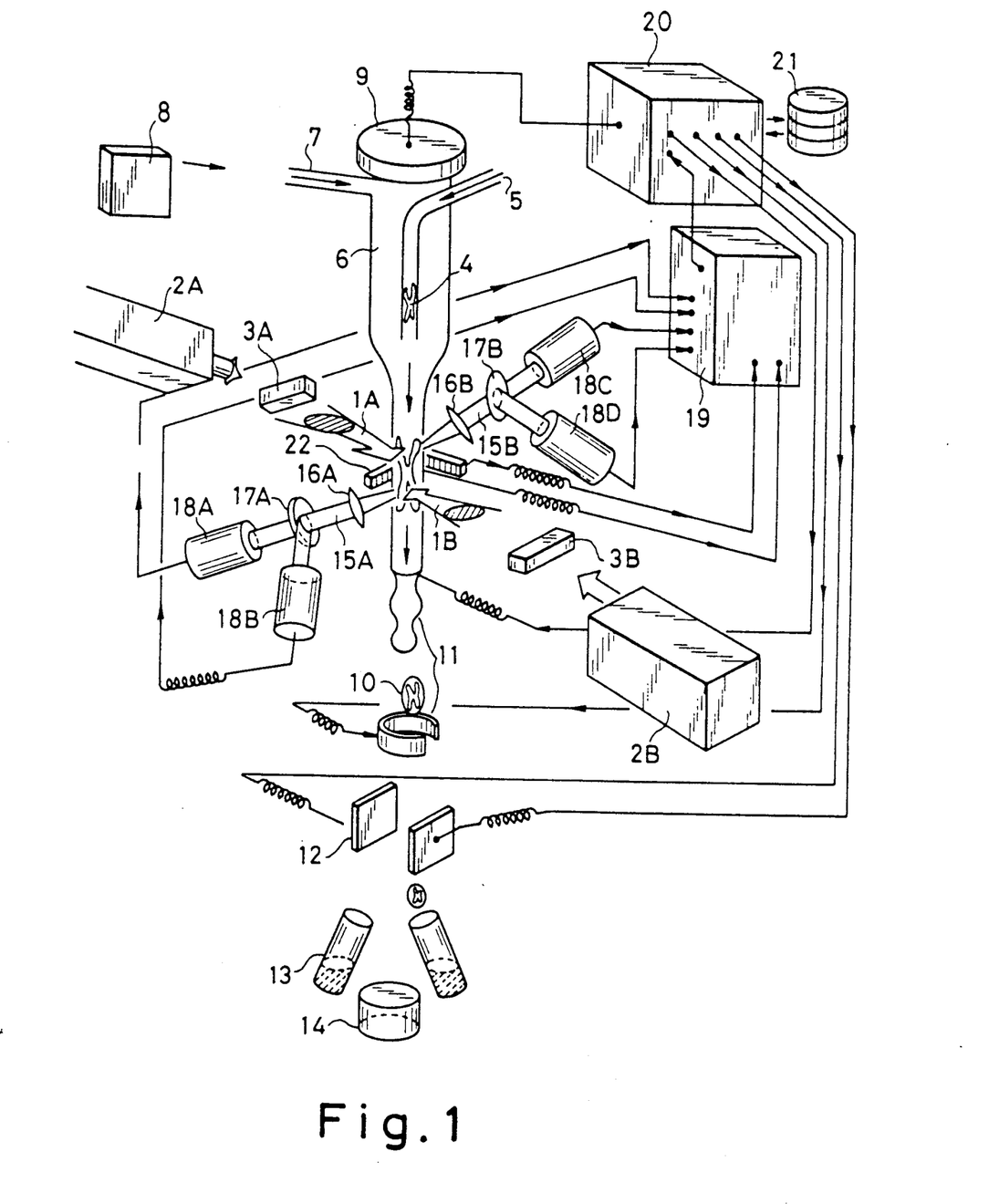
FIG. 1 is an explanatory diagram showing an embodiment of the present invention.

FIG. 1 illustrates an outline of an embodiment according to the present invention. This apparatus comprises a) a laser beam generating and shape-forming portion, b) a sample flowing portion, c) a water droplet sorting portion, d) a fluorescence detecting portion, e) a high-speed profile-pattern processor, and f) a central processing unit. The respective portions a) to f) of the present apparatus will be described in more detail hereinbelow.

The laser beam generating and shape-forming portions are composed of two sets of laser beam oscillators 2A and 2B for emitting laser beam 1A of ultraviolet rays and laser beam 1B of visible rays, respectively, and two sets of optical systems 3A and 3B such as lenses for forming a laser beam with traverse section being a submicron in thickness and several hundreds μm in width, respectively. In the above construction, when two sets of the laser oscillators 2A and 2B are employed, laser beams having different wavelengths can be used as light sources, so that it is possible that two kinds of DNA specific dyes can be combined for labelling chromosome or cell.

The sample flowing portion b) is composed of a flow chamber 6 for changing a flow stream 5 containing chromosomes or cells 4 into sheath-like laminar flow, a sheath liquid 7 for positioning the flow stream 5 at the center of the flow, a pressure device 8 for maintaining a high speed of the flow, and a piezoelectric vibrator 9 for affording a minute vibration to the flow chamber 6. When the piezoelectric vibrator 9 is minutely vibrated, droplets are formed in every second coincidently with the frequency of the piezoelectric vibrator.

The water droplet sorting portion c) is composed of a droplet charging unit 11 for applying positive or negative electric charge to a droplet 10 containing one cell or chromosome, deflection plates 12 for separating droplets by deflecting the falling droplets 10 from the direction along which the droplets drop by means of a force of electric field, a droplet capturing device 13 for capturing the droplets 10 which have been deflected by the deflection plates 12, and a container 14 for undeflected droplets which collects waste liquid In order to charge droplets, weak electric current is applied between an electrode which is in contact with the flow stream at the position of a nozzle in the flow chamber and a ring-shaped electrode encompassing the droplets 10. An apparatus described herein is the same as a conventional cell sorter except the optical systems 3A and 3B. (L. A. Herzenberg et al.: "Fluorescence-activated cell sorting", Scientific American, pp. 108–117, March, 1976).

The fluorescence detecting portion d) is composed of lenses 16A and 16B for collecting fluorescences 15A and 15B emitted from labelled chromosomes or cells with a fluorescent material, dichroic filters 17A and 17B for dividing the collected fluorescence into spectra of two wavelength bands, and several photomultipliers 18A–18D for detecting the fluorescence and converting the results detected into current.

The high-speed profile-pattern processor 19 contains a circuit for shaping and amplifying an output pulse waveform from the photomultiplier 18, a circuit for sampling the pulse waveforms, an A/D converter for digitalizing a value of voltage sampled, a mass storage element, and a comparator.

The central processing unit 20 contains a microcomputer, a cathode ray tube display, a printer, and a keyboard. Furthermore, a large auxiliary storage 21 is connected to the central processing unit 20.

It is to be noted that a temporal disperser photometer 22 is a device for measuring a rough two-dimensional shape of flowing chromosome or cell.

The operation of the present embodiment having the construction shown in FIG. 1 will be described hereinbelow.

The sheath liquid 7 made of physiological saline is fed to the flow chamber 6 by means of the pressure device 8, and at the same time the sample liquid 5 in which an object to be detected, that is, chromosome or cell 4, floats is fed into the flow chamber 6 at a position of the central axis so as to wrap the sample liquid in the sheath liquid. In this case, the cells or chromosomes being the object to be detected have been previously stained with a fluorochrome material. In order to maintain the cells at the center, a flow ratio between the sheath liquid and the sample liquid is suitably selected.

The flow chamber 6 is minutely vibrated by the use of the piezoelectric vibrator 9, and a droplet containing a cell or a chromosome is allowed to drop. The aqueous suspension flowing in the nozzle portions is irradiated with such laser beams 1A and 1B focussed by means of an optical system which will be described in detail in FIG. 2. The fluorescence emitted from the fluorescent material in the chromosomes or cells, which have been previously labelled, is collected by the lenses 16A and 16B, the fluorescence thus collected is separated by the dichroic filters 17A and 17B into its spectral components, and an optical signal is detected by means of the photomultipliers 18A–18D to convert it into an electric signal. A detected signal from the photomultipliers 18A–18D is analyzed by utilizing the high-speed profile-pattern processor 19, the central processing unit 20, and the large auxiliary storage 21 so as to output such a signal whether or not the detected cell or chromosome should be sorted from the central processing unit 20.

When the signal from the central processing unit 20 is a sorting signal, electric charge is applied to the droplet 10 by means of the droplet charging unit 11, and the droplet is attracted towards such deflection plate 12 having the sign of charge which is opposite to that given to the droplet 10 when the droplet passes through the deflection plates 12, whereby droplets containing chromosome or cell of a specific type are selectively collected in the water droplet capturing device 13. Droplets which should not be sorted are collected in the container 14 for undeflected droplets.

Next, a manner how a focussed laser beam is formed will be described in detail hereinbelow.

Figure 2:
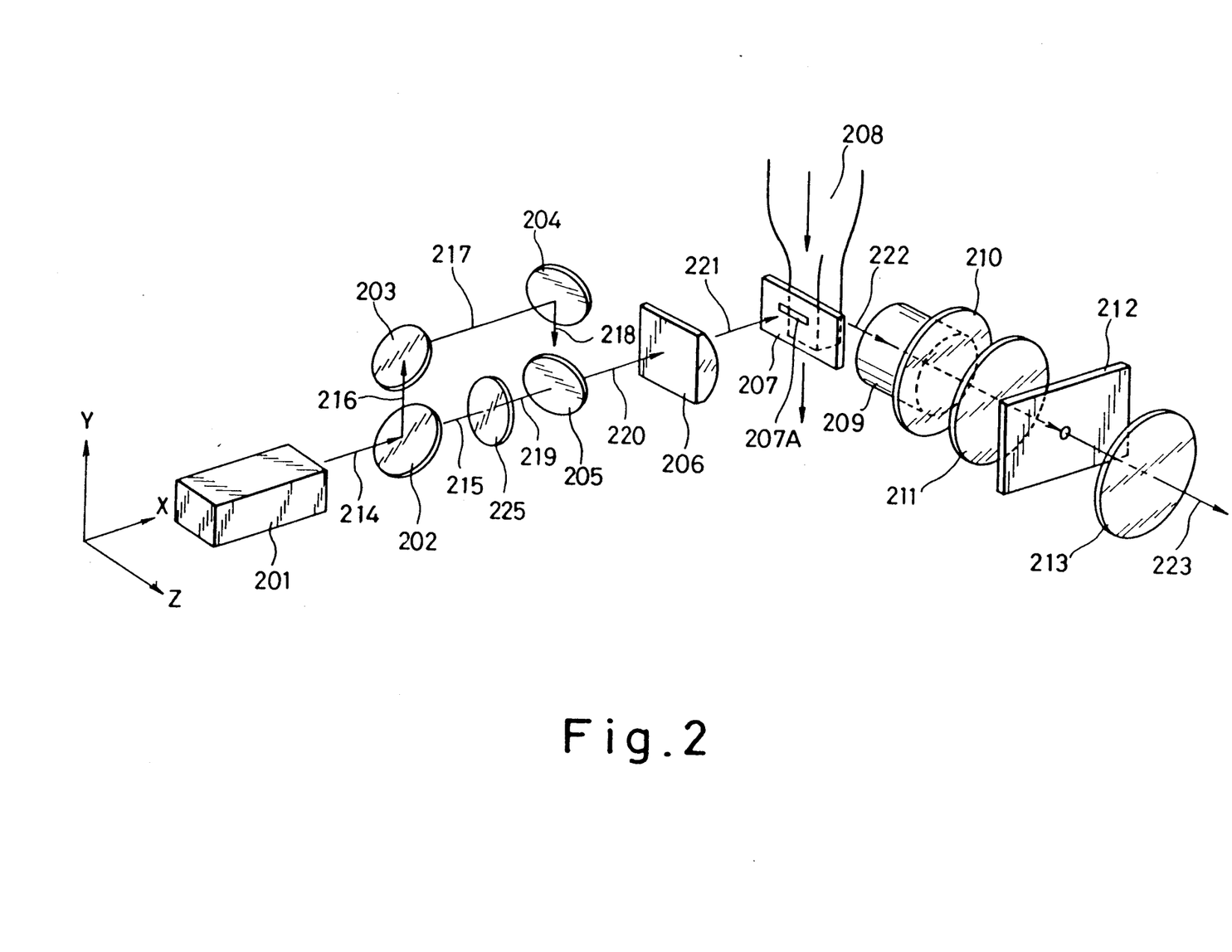
FIG. 2 is a perspective view showing an optical system which generates a laser beam and is used in the embodiment of the present invention in FIG. 1.

FIG. 2 is a view showing details of the optical system for forming laser beam according to an embodiment of the present invention wherein reference numeral 201 designates a laser oscillator emitting continuous visible radiation or ultraviolet radiation, the diameter of a laser beam is about 1.6 mm, 202 a beam splitter (half mirror), 203 and 204 mirrors, 205 a beam splitter (half mirror), 206 a cylindrical lens, 207 a shade having a slit 207A of several hundreds $\mu m$ in breadth and about 1 $\mu m$ in width, and 208 the flow chamber shown in FIG. 1 which forms a sample liquid containing cells or chromosomes into a sheath-like laminar flow, respectively. Chromosomes or cells pass through the flow chamber 208 along the central axis thereof. An external form of a nozzle portion of the flow chamber 208 is a regular octagon In this case, a diameter of a pore defined on the nozzle portion for permitting cells or chromosomes to pass therethrough one by one is about 200 $\mu m$. In the present embodiment, since the cells or chromosomes passing through the pore of the nozzle portion are irradiated with a laser beam, a material constructing the nozzle portion is selected from materials, for example, synthetic quartz through which the laser beam can pass uniformly. In this case, since an oil or glycerine for oil immersion is applied to a gap between the regular octagonal outer wall of the nozzle portion and the slit 207, the outer wall of the nozzle portion is in close contact with the slit. Furthermore, reference numeral 209 designates an objective lens, 210 an interference filter such as a long pass filter, 211 a convex lens, 212 a pinhole, and 213 a dichroic filter, respectively.

Next, irradiation of laser beam in the optical system shown in FIG. 2 as well as emission of fluorescence will be described in detail hereinbelow.

First of all, a laser beam 214 is emitted from the laser oscillator 201. In this case, a direction along which the laser beam 214 proceeds is set to be the X-axis The Y-axis is in a direction along the centerline of an axis through which cells or chromosomes flow at a high-speed in the flow chamber 208. The regular direction of the Y-axis is opposite to that along which the chromosomes or cells flow. The Z-axis is determined in a right-hand system composed of the X-, Y-, and Z-axis The laser beam 214 emitted along the regular direction of the X-axis is divided into a passing laser beam 215 and a reflected laser beam 216 by means of the beam splitter 202. The reflected laser beam 216 is reflected by the mirror 203 to form a laser beam 217, and the laser beam 217 is further reflected by the mirror 204 to form a laser beam 218. The passing laser beam 215 is in parallel to the reflected laser beam 217.

The passing laser beam 215 passes through a neutral filter 225 between the beam splitters 202 and 205 to form a laser beam 219. The neutral filter 215 is a filter for adjusting a beam intensity of the laser beam 218 so as to be equal to that of the laser beam 219 in the beam splitter 205. In this situation, if the beam intensity in these two laser beams is not equal to each other, contrast in beam intensity in crest and trough of a fringe pattern as mentioned hereinbelow becomes weak In the beam splitter 205, the laser beam 218 interferes with the laser beam 219 to form a laser beam 202 of a pattern of several fringes Such a method in which an optical system is composed of the beam splitters 202 and 205 as well as the mirrors 203 and 204, and two laser beams 218 and 219 are allowed to interfere with each other is generally called as the Mach-Zehnder interference method The optical axes of the beam splitters 202 and 205 intersect the optical axes of the mirrors 203 and 204 to form a parallelogram.

An extent of a laser beam 220 in the direction of the Y-axis is reduced by means of the cylindrical lens 206, so that it becomes a laser beam 221 having a high beam intensity distribution along the direction of the Z-axis. The laser beam 221 passes through a slit 207A, so that it transforms from a laser beam of a high intensity having a pattern of several fringes into a laser beam having a pattern of only one fringe with high intensity. Such chromosomes or cells flowing along the central axis of the flow chamber 208 are irradiated with the laser beam having a pattern of substantially only one fringe and light 222 containing lateral scattered light and fluorescence is emitted. The emitted light 222 is collected by means of the objective lens 209. The fluorescence passes through the interference filter 210, while the lateral scattered light does not pass through the interference filter 210.

The fluorescence appears on the side of a longer wavelength than that of the laser beam for excitation. When the fluorescence is focussed by the convex lens 211 and allowed to pass through the pinhole 212, only the fluorescence emitted from the chromosomes or cells is obtained, while outwardly scattered light and noisy light are interrupted by means of the pinhole 212. The latter fluorescence is further spectrally separated by the use of the dichroic filter 213 into the one having a specified wavelength band.

Figure 3:
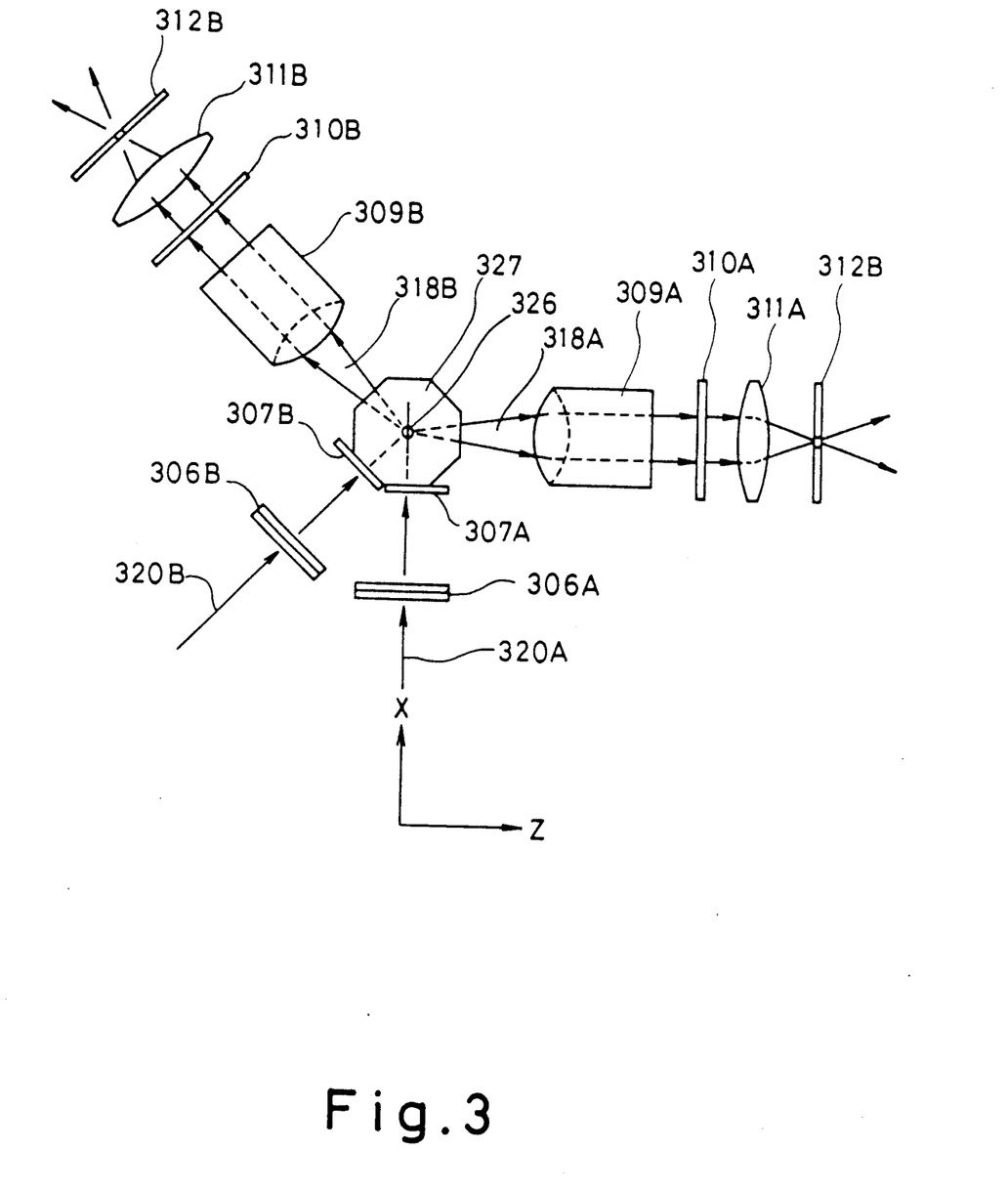
FIG. 3 is a schematic view showing the flow chamber and the fluorescence measuring system in FIG. 1.

FIG. 3 is a constructional view of a flow chamber and a fluorescence photometric system wherein the X- and Z-axis have the same meaning as those appeared in the description of FIG. 2. Reference numerals 306A and 306B designate cylindrical lenses, and 307A and 307B shades each having an opening, respectively. A dimension of the opening is the same size as that of the slit 207A shown in FIG. 2. A flow stream containing chromosomes or cells flows at a high-speed through a pore 326, and a diameter of the pore 326 has already been described in the description as to the nozzle portion of FIG. 2. A material and an outer shape of a nozzle portion 327 in the flow chamber are the same as those of the flow chamber 208 shown in FIG. 2. The focal points of objective lenses 309A and 309B coincide with the central axis of the pore 326 in the flow chamber Interference filters 310A and 310B are allowed to pass only fluorescence therethrough. The focal points of convex lenses coincide with the positions of pinholes 312A and 312B, respectively. The pinholes 312A and 312B function to pass through only fluorescence emitted from chromosomes or cells.

Next, irradiation of laser beam in the optical system shown in FIG. 3 and emission of fluorescence will be described hereinbelow.

In FIG. 3, chromosomes or cells are irradiated with two laser beams 320A and 320B having different wavelengths from each other. This is because two or more fluorescent probes are employed For the simplicity, it is assumed that reference numeral 320A designates a laser beam of ultraviolet rays, and reference numeral 320B designates a laser beam having a wavelength of a visible region. The laser beam 320A proceeds to the central axis of the pore 326 along the direction of the X-axis, while the laser beam 320B proceeds to the central axis of the pore 326 at an angle of 45° defined by the laser beam 320B and the X-axis. In this case, the laser beam 320A is in the same plane as that of the laser beam 320B. After the laser beams 320A and 320B having a pattern of several fringes formed by interference of these laser beams passed through the cylindrical lenses 306A and 306B, laser beams with several fringes have high beam intensities in horizontal direction such as thin thickness beam. Furthermore, after these laser beams passed through the shades 307A and 307B each having a slit, the intensity of one central fringe beam becomes much higher than those of the other fringe beams The laser beam having a thin thickness in intensity which has passed through a slit is hereinafter referred to as "linear laser beam".

When chromosomes or cells flowing through the pore 326 opened along the central axis of the nozzle portion 327 of the flow chamber are irradiated with two laser beams, forward scattered light as well as fluorescence 318A and 318B are emitted.

In this case, such beam emitted as a result of the irradiation of cells or chromosomes with laser beam is observed in the rectangular direction. This is because fluorescence to be measured appears on the side of a longer wavelength than that of excited light due to irradiation with laser beam and further its light intensity is weak. Emitting beams 318A and 318B from the cells or chromosomes become parallel beams when the beams pass through the lenses 309A and 309B. When these two beams pass through the interference filters 310A and 310B, there remains only fluorescence. When two fluorescent beams pass through the convex lenses 311A and 311B, they are converged and pass through the pinholes 312A and 312B. Thereafter, the fluorescence is spectrally separated by the dichroic filter, the separated fluorescence is detected by means of the photomultiplier, and the signal detected is analyzed to sort specific chromosomes or cells.

Figure 4A:
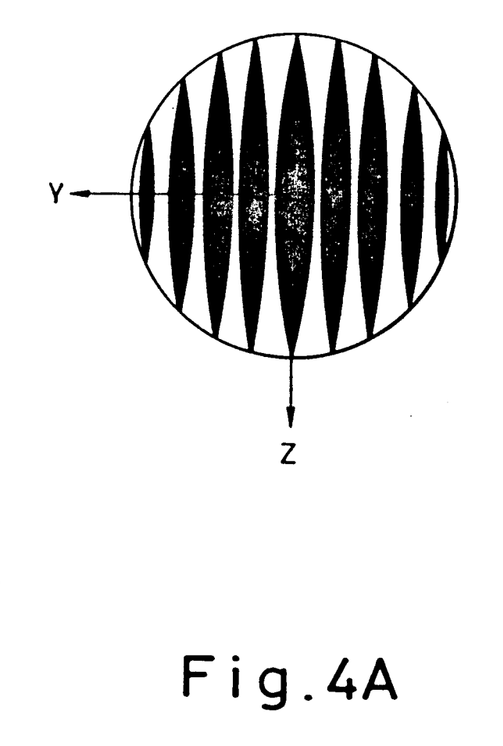
FIGS. 4A and 4B are explanatory diagrams showing a fringe pattern of a laser beam and an intensity distribution of an interference laser beam, respectively.
Figure 4B:
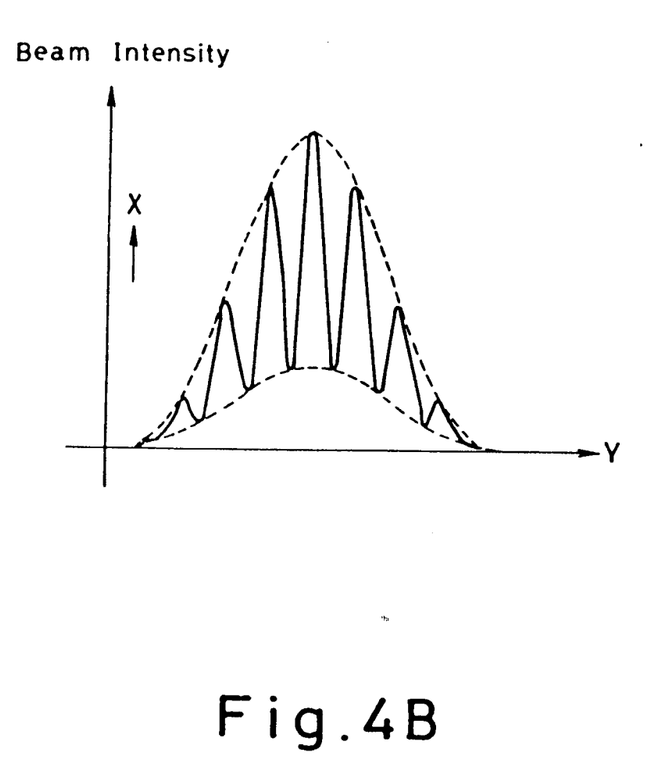

FIGS. 4A and 4B show a fringe pattern of laser beam and an intensity distribution of the laser beam at traverse section wherein FIG. 4A is an enlarged view showing a vertical stripe-like fringe pattern appeared in a circle having a diameter of about 1.3 mm which exhibits an outer boundary of an extent where the laser beam emitted from a laser beam source extends. In FIG. 4A, the portions darkened in the circle indicate portions where a beam intensity is high, the direction of a vertical fringe corresponds to that of the Z-axis, and the perpendicular direction to the vertical fringes is considered to be that of the Y-axis, i.e., the direction of a flowing axis along which chromosomes or cells flow.

FIG. 4B illustrates a beam intensity distribution of the laser beam in the direction of the Y-axis, the laser beam having the fringe pattern shown in FIG. 4A. From FIG. 4B, it is found that several linear laser beams having a high beam intensity in the direction of the X-axis proceed in parallel to each other.

Figure 5:
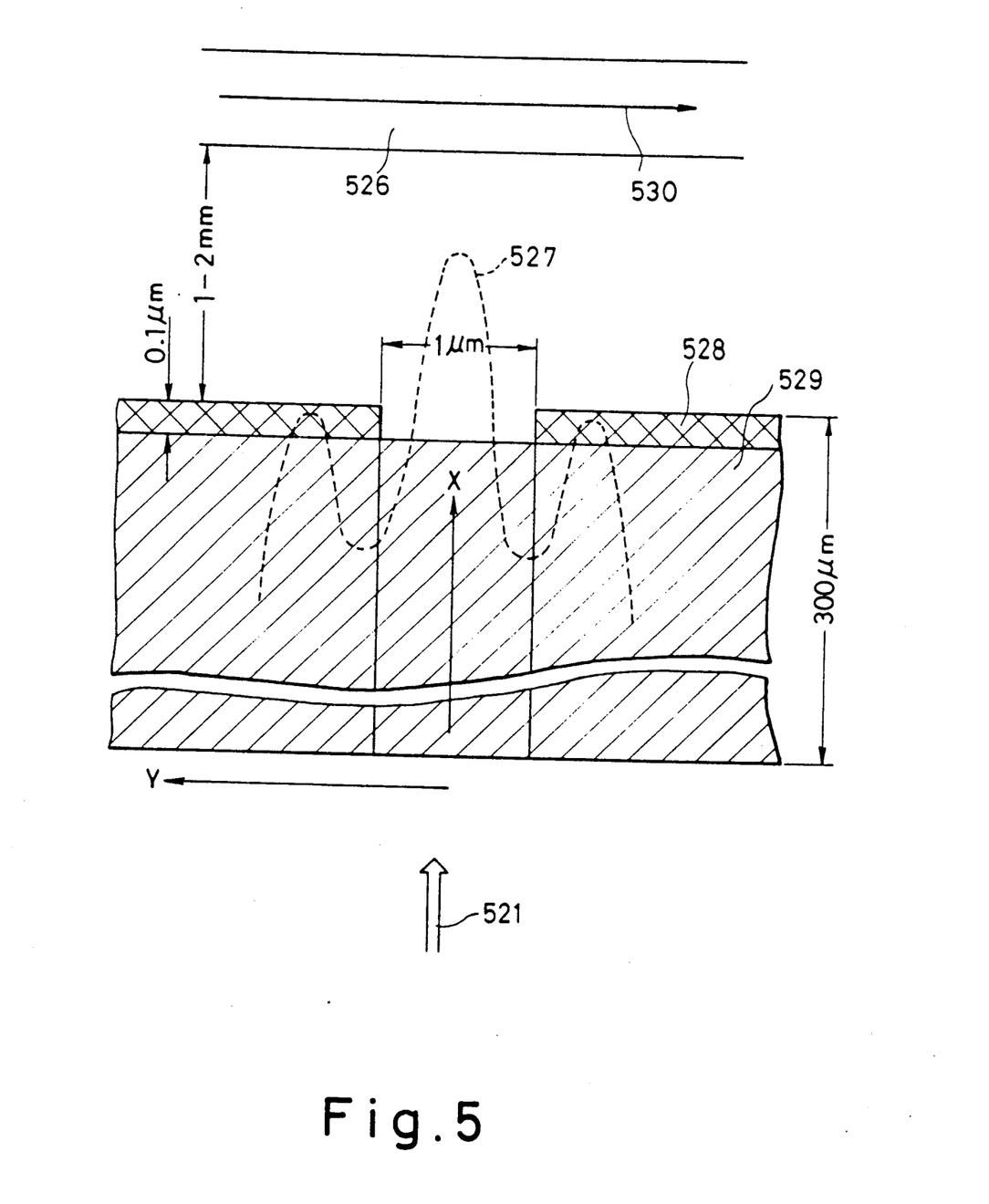
FIG. 5 is an explanatory diagram illustrating a method for generating a linear laser beam.

FIG. 5 is an explanatory view for a method for forming a linear laser beam having substantially one high beam intensity and a thin thickness from a laser beam having a pattern of several fringes The method for forming a linear laser beam relates to the one in which a laser beam having a pattern of several fringes is allowed to pass through a substantially linear slit.

In this embodiment, a shade having a slit is composed of a slit substrate 529 made of synthetic quartz having a thickness of about 300 $\mu$m and a chromium coating layer 528 having a thickness of about 0.1 $\mu$m which has coated the slit substrate 529. The slit through which a laser beam 521 passes is opened in accordance with a publicly known photo-etching technique, so that an opening having a thickness (thickness in the Y-axis direction) of 1 $\mu$m and a breadth (length in the Z-axis direction) of about several hundreds $\mu$m is obtained. In this case, a thickness of the slit is substantially determined by a half-value width of the fringe pattern and a wavelength of the laser beam, and it may be determined within a range of 0.6-1.5 $\mu$m. Furthermore, in order that a flux portion of a flow chamber through which chromosomes or cells flow is easily irradiated with linear laser beam, a breadth in the slit is defined wider than a diameter of a pore (50-200 $\mu$m) in the nozzle portion of the flow chamber, and it is usually within a range of 50-300 $\mu$m.

A distance between the shade having a slit and the inner wall of the nozzle portion of the flow chamber is determined to be 1-3 mm. In this case, a laser beam 521 which has passed through a cylindrical lens to possess a fringe pattern of the beam intensity in its breadth direction has a beam intensity distribution represented by beam 521 which has proceeded in the direction of the X-axis passes through a slit having a thickness of 1 $\mu$m, only such a linear laser beam having a pattern of substantially single fringe of a highest beam intensity remains among laser beams each having a pattern of several fringes. Chromosomes or cells which flow through the pore 526 of the nozzle portion of the flow chamber at a high speed along a flow axis 530 of the flow chamber are irradiated with the laser beam which has passed through the aforesaid slit.

As a result, a thin laser beam having a thickness of a submicron order is formed. In this case, it is required for forming a linear laser beam whose intensity is high that accuracy of a cylindrical lens and a breadth of the slit have been sufficiently adjusted to correct According to the manner as described above, it is possible to narrow down a thickness of such a linear laser beam up to about half the wavelength of a laser beam A problem in the manner of the present embodiment is in that a linear laser beam emitted from the linear slit is diffracted at an opening of the slit.

The case of the Fraunhofer diffraction which is observed in the event where a distance between a slit and a laser beam source and between a slit and a point to be irradiated in the flow axis are comparatively long will be considered with taking such fact that an opening of the slit is rectangular into consideration (for example, see Max Born & Emil Wolf "Principles of Optics", Pergamon Press., 1975). In the case of the Fraunhofer diffraction, a diffracted intensity I is generally given as follows:

$$I \propto \left(\frac{\sin u_1}{u_1}\right)^2 \left(\frac{\sin u_2}{u_2}\right)^2$$

wherein $u_1$ and $u_2$ are dependent upon a thickness and breadth of a slit, a wavelength of laser beam, and a distance from a slit to a point to be irradiated and to a laser beam source, but they depend principally upon an angle of diffraction.

Figure 6:
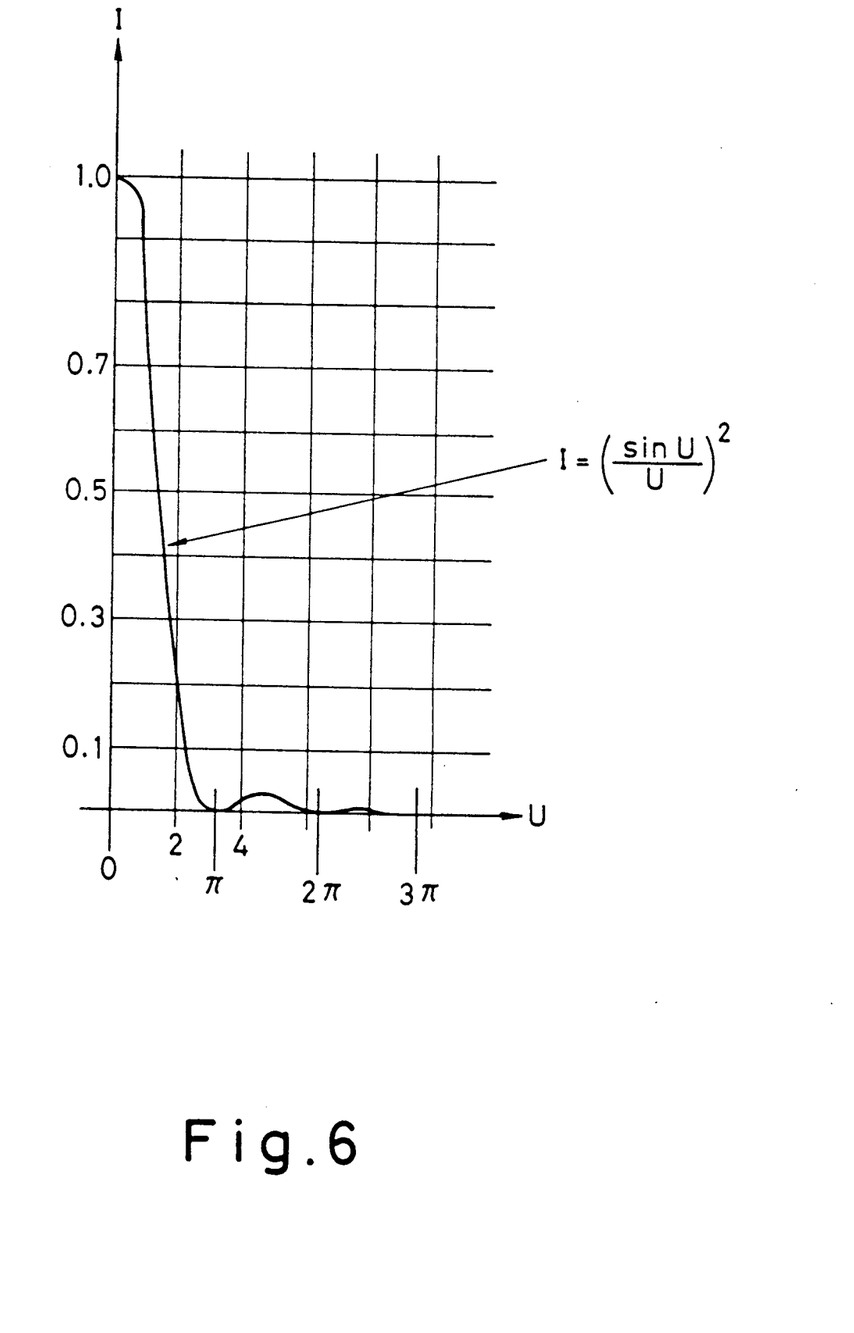
FIG. 6 is a graphical representation illustrating an intensity distribution of a diffracted beam due to a rectilinear slit.

FIG. 6 shows an intensity distribution of diffracted light by means of a rectilinear slit. If the slit is linear, one of $u_1$ and $u_2$ is 0, so that the diffracted intensity I in this case is given as follows:

$$I \propto \left(\frac{\sin u}{u}\right)^2$$

wherein u is dependent upon a width of the slit, an angle of diffraction, a wavelength of laser beam, and a distance between a slit and the points to be irradiated and between a slit and a laser beam source An intensity of diffracted light in the case where the slit is a rectilinearly opened slit has such a distribution which is substantially proportional to square of the curve shown in FIG. 6.

From FIG. 6, it is understood that the laser beams are composed of a linear laser beam whose intensity is the highest in the horizontal direction (the Z-axis) being perpendicular to that along which the laser beam propagates and another laser fringe beams which are parallel to the former laser beam and are very weak in intensity.

Accordingly, one laser beam having a wide breadth and a thin thickness among laser beams which proceed in the onward direction excites a fluorescent material within the narrow strip of local portions in chromosomes or cells flowing in a flow chamber at a high-speed along the flow axis thereof. Since such another laser beam which is in parallel to the laser beam having the highest beam intensity exhibits a weak beam intensity, it does not contribute to the excitation of fluorescent material so much. Even if there is fluorescence emitted as a result of irradiation of laser beam, such fluorescence becomes background noise.

Such a case where chromosomes are irradiated with the linear laser beam formed as mentioned above will be considered hereinbelow.

Figures 7A, 7B:
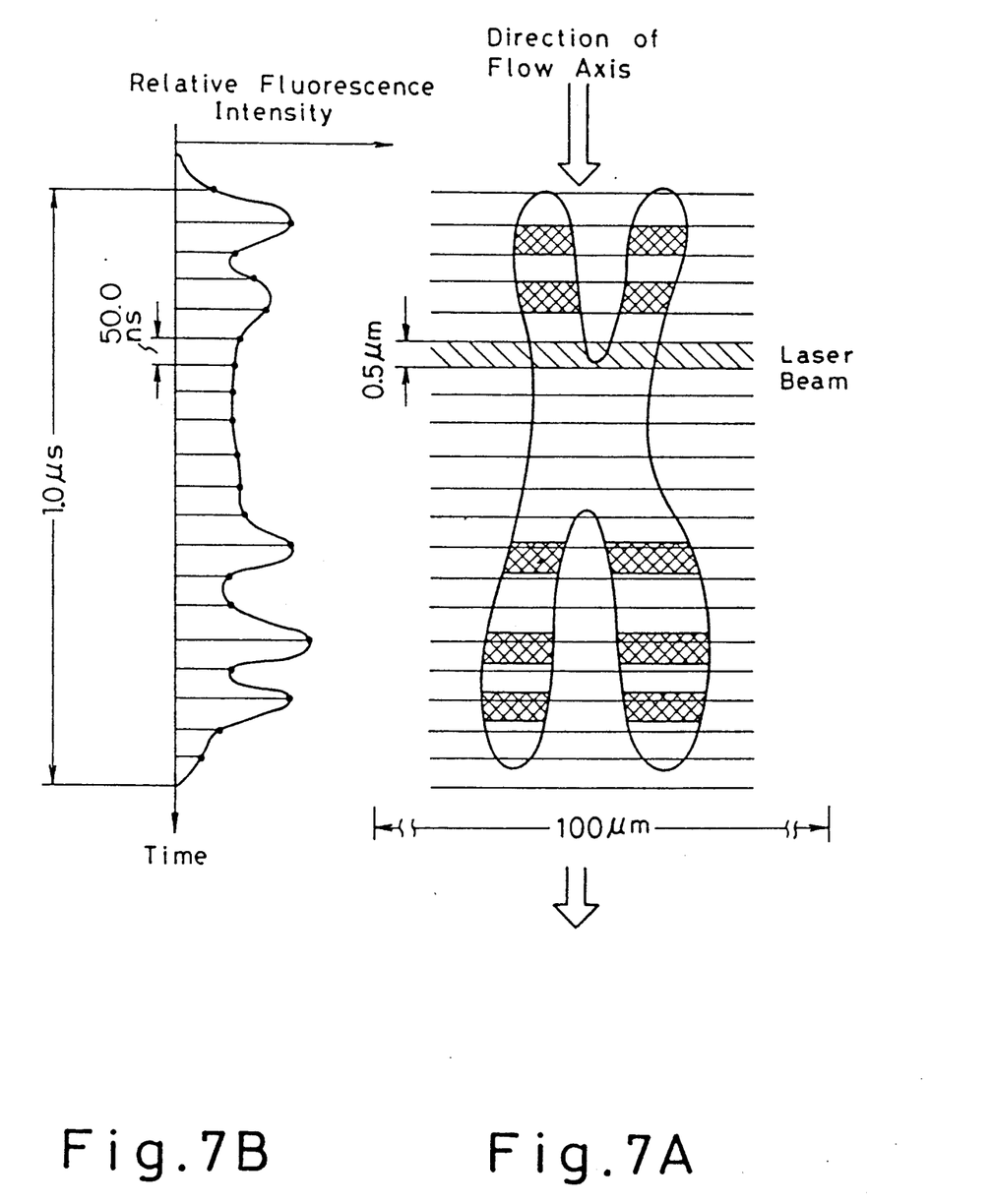
FIGS. 7A and 7B are explanatory diagrams showing a band pattern of a chromosome and a fluorescent profile-pattern, respectively.

FIG. 7A is an explanatory view of chromosome showing a situation where as an example, a chromosome having an entire length of 10 μm is allowed to flow through a nozzle diameter of 100 μm of a flow chamber at a flow velocity of 10 m/sec., in the direction from the upper part to the lower part in FIG. 7A. In this figure, a hatched portion indicates a section of a linear laser beam having a thickness of 0.5 μm, and a cross-hatched portion indicates a band pattern of the labelled chromosome with a fluorescent material.

FIG. 7B is a graphical representation indicating a change with time in respec. of a fluorescent intensity emitted from the chromosome shown in FIG. 7A wherein the abscissa indicates a time elapsed from the beginning of irradiation of the chromosome with a linear laser beam, while the ordinate indicates a relative fluorescent intensity to be detected, and in this case, since the entire length of the chromosome is 10 μm and the flow velocity is 10 m/sec., the elapsed time is 1 μsec.

Since the linear laser beam has a thickness of a submicron order, a chromosome is excited at only a strip of submicron width. In this case, fluorescent luminous energy irradiated is proportional to an amount of the fluorescent material which is contained in a strip of the chromosome. The fluorescence detected in a photomultiplier is converted into an analog value which varies sequentially in a continuous manner, and then the value is output This analog signal is converted into a digital value which can be represented in 8 or 16 bits by sampling the analog signal at an interval of 50.0 nsec., with the use of a digital/analog (A/D) converter. In this case, an entire length of chromosome is 10 μm and a width of liner laser beam is 0.5 μm, so that the resultant output of the A/D converter is represented by a twenty-dimensional vector with respect to individual chromosome or cell. While a flow velocity of chromosome and a sampling time interval therefore are considered to be 10 m/sec., and 50.0 nsec., respectively, for the sake of simplicity. An actual flow velocity of chromosome is far rapid, and a sampling time interval is far short. Accordingly, a series of the digital values obtained every moment becomes a tens-dimensional vector in general. This tens-dimensional vector is reflective of local differences in fluorescence intensity of chromosome or cell. In this connection, such a tens-dimensional vector is referred to herein as "fluorescence profile-pattern".

Figure 8:
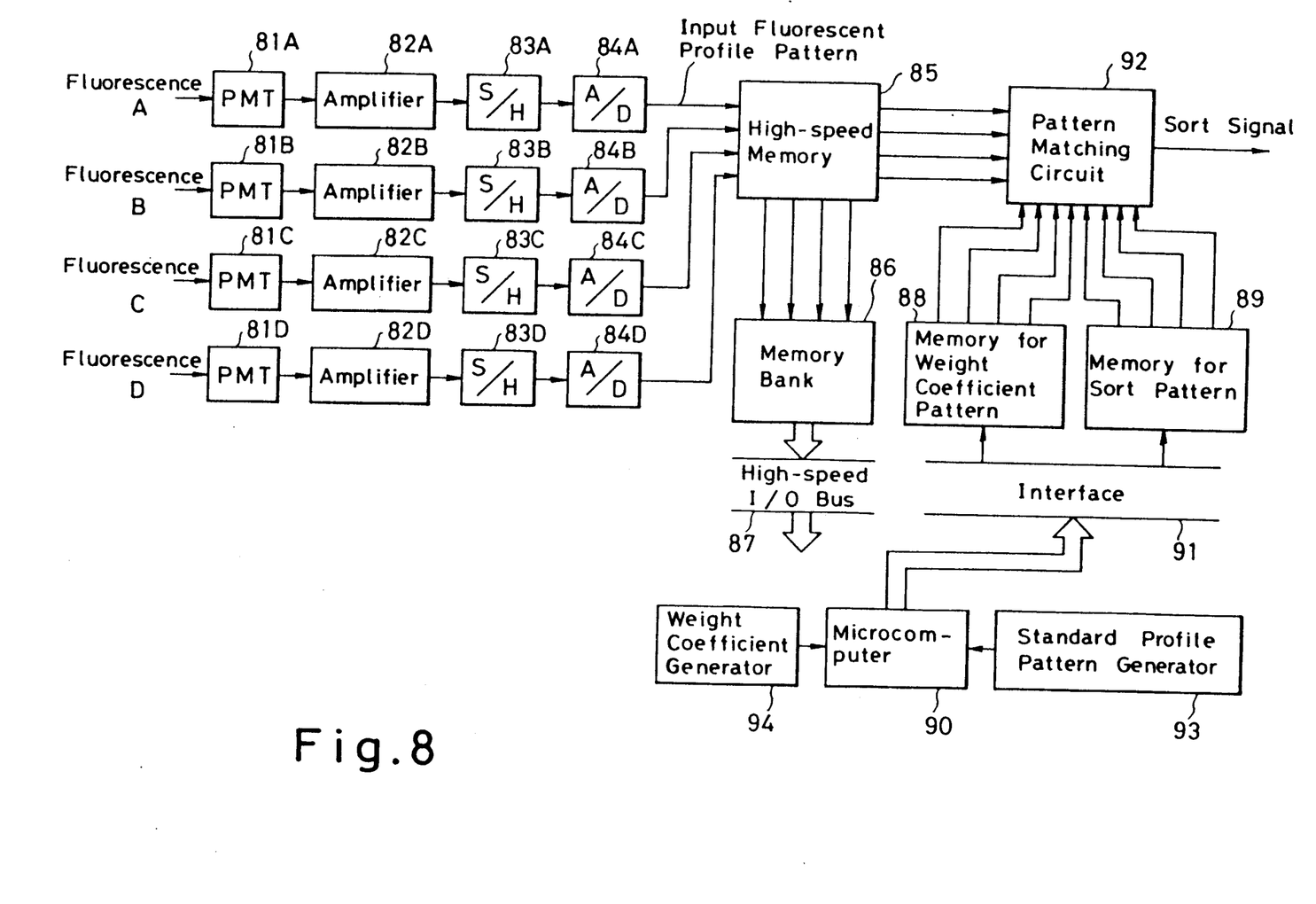
FIG. 8 is a block diagram showing a schematic constructional example of an electronic circuit for analyzing a fluorescent profile-pattern.

FIG. 8 is a block diagram showing a constructional example of an electronic circuit which identifies type of chromosome or cell by analyzing a fluorescence profile-pattern wherein reference numerals 81A to 81D designate photomultipliers (PMT), 82A to 82D amplifiers, 83A to 83D sample and hold circuits (S/H), 84A to 84D analog-digital converting circuits (A/D), 85 a high-speed memory, 86 a memory bank, 87 a high-speed I/O bus, 88 a memory for weight coefficient pattern, 89 a memory for sort pattern, 90 a microcomputer, 91 an interface, 92 a pattern matching circuit, 93 a standard profile-pattern generator, and 94 a weight coefficient generator, respectively.

Next, operation of the electronic circuit shown in the block diagram of FIG. 8 will be described hereinbelow.

Emitting fluorescent beams A and B obtained in the case when chromosomes or cells are irradiated with ultraviolet laser are detected by the PMT 81A and 81B, respectively. On the other hand, emitting fluorescent beams C and D when chromosomes or cells are irradiated with a visible light laser beam having a different wavelength with that of the above-mentioned ultraviolet laser beam are detected by the PMT 81C and 81D, respectively In this case, the PMT 81A to 81D are selected from ones suitable for a wavelength region of fluorescent beams A to D. Electric signals output from the PMT 81A to 81D are subjected to waveform shaping and amplified by means of the amplifiers 82A to 82D. Analog voltage signals from the amplifiers 82A to 82D are sampled by means of the S/H 83A to 83D at a time interval of from several tens nanoseconds to several hundreds nanoseconds to hold the resulting sampling values. In the A/D converters 84A to 84D, the voltage values which have been sampled and held are converted into digital values of 8 or 16 bits.

The tens-dimensional fluorescent profile-patterns thus obtained and digitalized are transferred to the high-speed memory 85. Such fluorescent profile-patterns of chromosomes or cells flowed in once sample-flow are stored in the memory bank 86. The memory bank 86 is a set of memory elements having a capacity sufficient for storing fluorescent profile-patterns, and a memory capacity of the memory bank is around several megabytes to several tens megabytes. Information stored in the memory bank 86 is properly output to the outside through the high-speed I/0 bus 87.

On one hand, the microcomputer 90 calls a set of standard profile-patterns necessary for identifying a specific type of chromosome or cell from the standard fluorescent profile-patterns generator 93 to store the standard profile-pattern in the memory 89 for sort pattern through the interface 91. Furthermore, the microcomputer 91 calls a set of weight coefficients from the weight coefficient generator 94 to store the weight coefficients in the memory 88 for weight coefficient pattern through the interface 91.

Then, in the pattern matching circuit 92, such a standard profile-patterns which have been multiplied by weight coefficients are compared with an input fluorescent profile-pattern from the high-speed memory 85 to identify the type of chromosome or cell, so that a sort signal is output from the pattern matching circuit 92 in only the case when one of the results compared as described above exceeds a threshold indicating a degree of coincidence of the patterns.

In a conventional cell sorter while identifying cells to be selected and collected in a real-time, identification has been performed on the basis of such result whether or not a height of a voltage pulse which is reflective of the total fluorescence intensity produced at the time when single cell traverses a laser beam is within a preset voltage level. In the apparatus of the present invention, the identifying method is based on a fluorescent profile-pattern of a tens-dimensional vector. However, since it is necessary to sort chromosomes or cells flowing at a high speed, a period of time being capable of allotting for identifying a type of chromosomes or cells in the present apparatus is only several tens microseconds. Accordingly, a comparatively simple procedure is utilized for identifying such a type.

In the present embodiment, since a width of laser beam is narrow, it may be considered that a fluorescent profile-pattern is influenced by not only the amount of fluorescent material contained in the narrow strip of local portions, but also an inclination of chromosomes or cells flowing.

For this reason, such standard profile-patterns in the case where chromosomes or cells flow with several inclinations are previously estimated and they are preset at the pattern matching circuit. If such profile-patterns of chromosomes with slightly inclined have not been prepared, there is a possibility of missing chromosomes or cells to be selected and collected.

In order to obtain a standard profile-pattern of flowing chromosomes or cells with an inclination, the rotating state in the three dimensional space of chromosomes or cells is determined.

Figure 9:
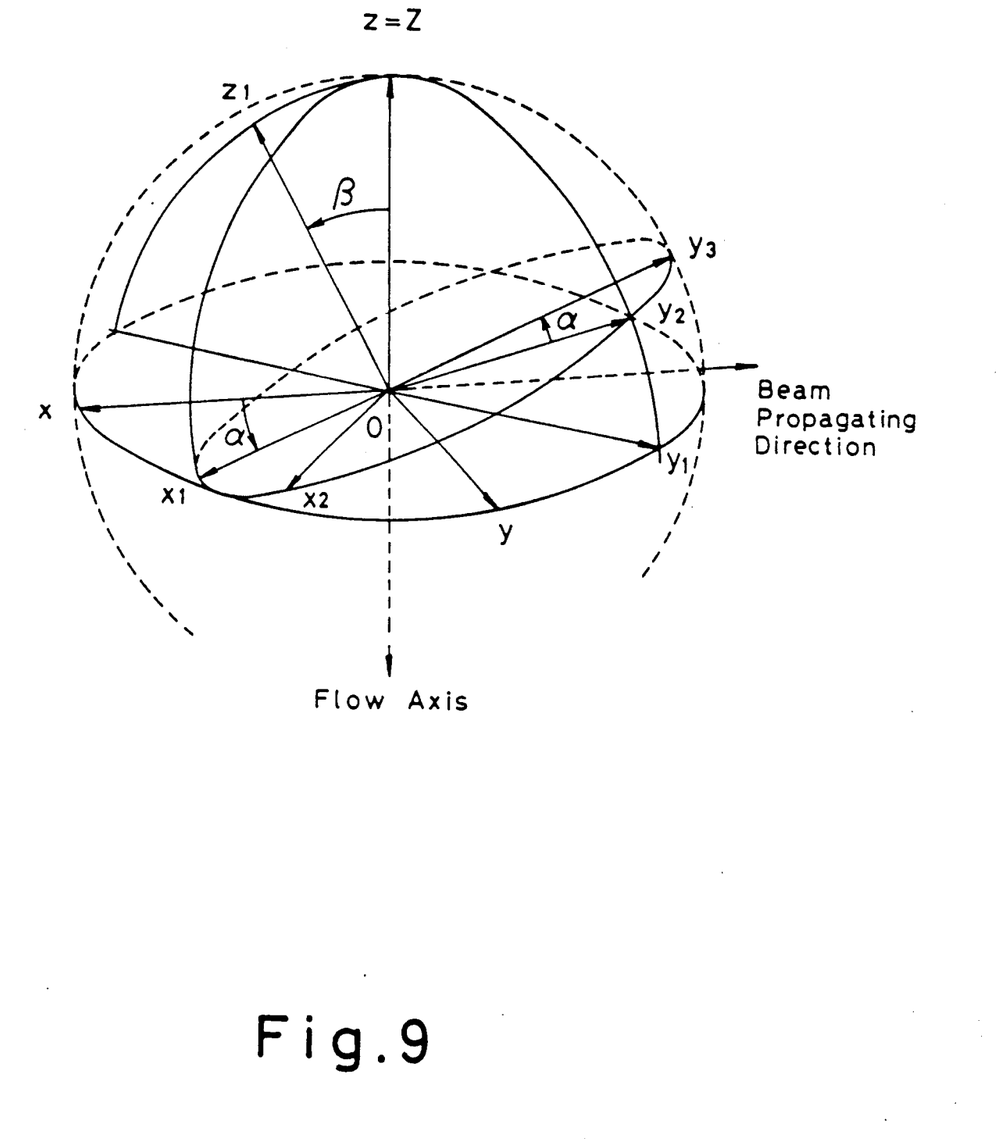
FIG. 9 is an explanatory diagram illustrating a relationship between Eulerian angles and rotational coordinates axes.

FIG. 9 is a graphical representation indicating a relationship between the Eulerian angles and the rotational coordinate axes wherein a direction opposite to that along which a floating liquid containing chromosomes or cells flows is considered to be a positive direction of the z-axis, the x- and y-axis exist in a plane perpendicular to the z-axis, a direction opposite to that along which a laser beam propagates is determined as the direction of the x-axis, and the y-axis direction is determined in such that the x-, y- and z-axis construct a right-hand system. If origin of the rectangular coordinate axes is assumed to be a point of intersection of a flow axis and the central axis of the laser beam, the spatial coordinate axes may be expressed as (0; x, y, z). When a substance rotates around the z-axis by an angle $\alpha$ radian, the coordinates axes become (0; $x_1$, $y_1$, z). Then, when the substance rotates around the $x_1$-axis by an angle $\beta$ radian, the coordinates axes become (0; $x_1$, $y_2$, $z_1$). Furthermore, when the substance rotates around the $z_1$-axis by an angle $\gamma$ radian, the coordinates axes become (0; $x_2$, $y_3$, $z_1$). These three angles ($\alpha$, $\beta$, $\gamma$) are called as the Eulerian angles.

For example, the Eulerian angle ($\alpha$, $\beta$, $\gamma$) are required for determining a rotating state of flowing chromosomes. In this connection, since the chromosomes flow in the negative direction of the z-axis at a rate of several meters per second, the longitudinal axial direction of chromosome becomes a state where it extends substantially along the z-axis. Accordingly, an Eulerian angle which influences the most significantly a variation of standard fluorescent profile-pattern is considered to be angle $\beta$. According to circumstances, there is such a case when a chromosome flows in a condition where the longitudinal axial direction of the chromosome is inverted.

For this reason, standard fluorescent profile-patterns in the following rotational conditions are prepared:

Eulerian angles (0°, 0°, 0°), (0°, 180°, 0°), (0°, 30°, 0°), (0°, −30°, 0°), (0°, 150°, 0°), (0°, 210°, 0°), (0°, 30°, 30°), (0°, −30°, 30°), (0°, 150°, 30°), (0°, 210°, 30°), (0°, 150°, −30°) and (0°, 210°, −30°). Standard profile-patterns defined and specified by the above described rotational conditions have been previously inputted into a standard profile-pattern generator, and such standard profile-patterns are suitably called out in the pattern matching circuit to compare them with a fluorescent profile-pattern inputted, thereby to identify chromosomes or cells to be sorted.

Figure 10:
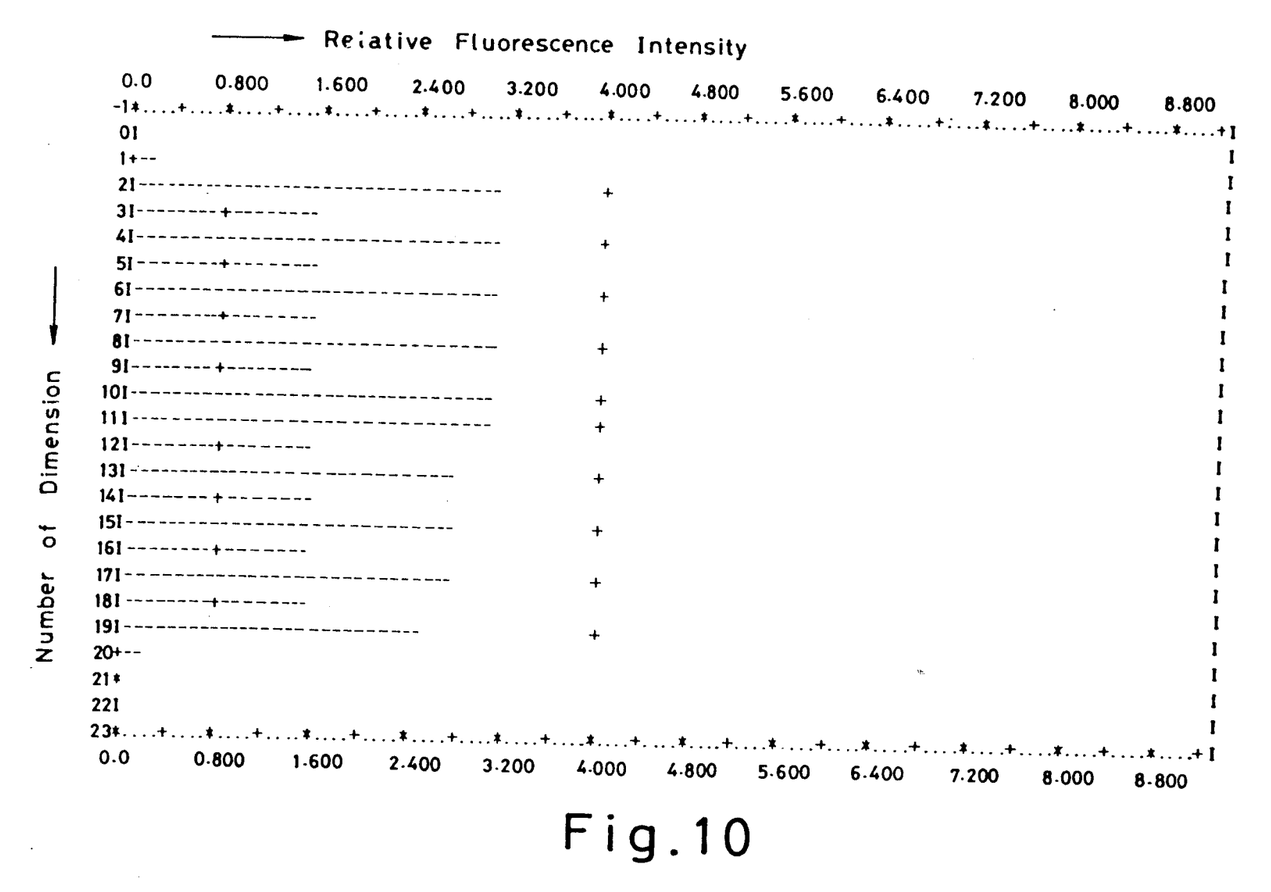
FIG. 10 is a diagram showing calculated results of computer simulation in respect of fluorescent profile-patterns of chromosome.

An example of results in computer simulation between a fluorescent profile-pattern in the case where chromosomes flow in an inclined posture and that of the case where chromosomes flow without any inclination is illustrated in FIG. 10.

FIG. 10 indicates calculated results of an expected fluorescence profile-pattern in the case where it is assumed that chromosome is a rectangular parallelepiped having a length of 9.0 μm, a breadth of 4.0 μm and a thickness of 2.0 μm and that a thickness of a very thin linear laser beam is 0.5 μm. In FIG. 10, the ordinate indicates the serial number of dimension indicating the number of times for measuring fluorescent intensities at different portions in one chromosome or cell The abscissa indicates the relative fluorescent intensity, and positive sign "+" indicates a fluorescent profile-pattern in the case where there is no rotational condition, i.e., an Eulerian angle is (0°, 0°, 0°). The profile-pattern indicates a fluorescent band pattern. A negative sign "−" bar graph indicates the fluorescent profile-pattern of the rectangular parallelepiped with the fluorescent band pattern oriented at an Eulerian angle (20°, 10°, 20°). As described above, when a plurality of standard fluorescent profile-patterns having different Eulerian angles are allowed to store in the apparatus according to the present invention, a type of cell or chromosome can be judged on the basis of such a fact whether or not at least one of indices which indicates the coincidence of the fluorescent profile-pattern with the standard fluorescent profile-patterns, exceeds a predetermined threshold.

Types of chromosome or cell differ from one another dependently upon types of organism (for example, human being, hamster, bird, fish and the like), and further fluorescent profile-patterns become different ones due to differences in fluorescence staining methods or fluorescent DNA specific dyes even in the same type of organism. Accordingly, there are substantially numerous standard profile-patterns of chromosome or cell. For this reason, it is impossible to always store all the standard fluorescent profile-patterns in the present apparatus.

However, types of organism to be identified, staining methods for fluorescent labelling, and in addition type numbers etc., of the chromosome or cell are known in advance in the case when a specific type of chromosome or cell is to be selected and collected in the apparatus of the present invention. Moreover, since a type of chromosome or cell to be selected and collected relates to only one type, the chromosomes or cells of the type can be sorted by comparing input profile-patterns measured consecutively with the standard profile-patterns of the type, even if the chromosomes or cells are passing through with inclinated postures in limited angles by means of the apparatus according to the present invention.

As described above, when such standard profile-patterns are suitably compared with a fluorescent profile-pattern inputted, a type of cell or chromosome to be sorted can be collected.

According to the present invention, only a fluorescence from a narrow strip of local portions which has been previously labelled by a fluorescent material can be measured in respect of a fluorescent intensity from such chromosomes or cells. Accordingly, there is no need for analysis of the fluorescence intensity obtained from several fringe patterns, so that only fluorescence intensities from local portions of individual chromosome or cell are measured in real-time and they are immediately utilized for sorting.

Furthermore, according to the present invention, chromosomes or cells are locally irradiated with a laser beam whose thickness is far thinner than a diameter of a chromosome or cell, an intensity of fluorescence emitted as a result of the irradiation is detected, and time sequential signals which are results of the detection are analyzed, so that chromosomes or cells of a specific type can be sorted and collected.

As described above, chromosomes or cells having different characters and functions can be analyzed and separated, so that changes in quantity or quality of such chromosomes or cells can be measured quantitatively and rapidly in accordance with the present invention. Therefore, the present invention can significantly contribute to various fields such as medical science, biology and the like.

What is claimed is:

1. An apparatus for identifying a chromosome or cell comprising:

means for flowing an aqueous suspension containing chromosomes or cells which have been previously labelled with fluorescent materials;

irradiation means for irradiating said chromosomes or cells, including a laser beam source for emitting a continuous laser beam, branching means for branching a part of laser beams emitted from said laser beam source and combining the branched laser beam with the emitted beams to form interference laser beams having a fringe pattern of lateral fringe perpendicular to a flow axis along which said chromosomes or cells flow, optical means for converting said interference laser beams having said fringe pattern into elliptical beams in which a direction of said flow axis is flat, and a slit for allowing only one bright portion of the interference fringe with the highest intensity at a central portion of the fringe pattern contained in said interference beams to pass therethrough to irradiate said chromosomes or cells with the laser beam containing only said single bright portion of the interference fringe;

fluorescence measuring means for measuring an intensity of fluorescence emitted from said chromosomes or cells due to said irradiation; and identifying means for detecting the signal output from said fluorescence measuring means to identify a chromosome or cell of a specific type, the signal output directly representing fluorescent profiles corresponding to figures of the chromosomes or cells.

2. An apparatus as claimed in claim 1, wherein a dimension of said slit in said flow axis direction is 0.6 to 1.5 $\mu$m with respect to the direction of said flow axis.

3. An apparatus as claimed in claim 1, wherein a breadth of said slit is 50 to 300 $\mu$m.

4. An apparatus as claimed in claim 1, wherein said irradiation means is provided with two laser beam sources.

5. An apparatus as claimed in claim 4, wherein said laser beams forming a crossing angle of 45° with each other in a plane perpendicular to said flow axis are emitted from said two laser beam sources.

6. An apparatus for identifying a chromosome or cell comprising:

a means for flowing a liquid containing chromosomes or cells at a high-speed;

a means for emitting light onto said chromosomes or cells flowing through said flowing means;

a fluorescence measuring means for measuring fluorescence-intensity emitted from a fluorescent material with which said chromosomes or cells have been previously labelled;

a discriminating means wherein a fluorescent profile-pattern obtained from variation of said fluorescent intensity with time is compared with a plurality of the preset standard fluorescent profile-patterns of chromosome or cell; and a sorting means for sorting said chromosomes or cells on the basis of the comparison of said fluorescent profile-pattern with said preset standard fluorescent profile-patterns by said discriminating means.

7. An apparatus as claimed in claim 6, wherein said standard profile-pattern includes a profile-pattern relating to a rotating condition of chromosomes or cells.

* * * * *